United States Patent [19]

Månsson et al.

[11] Patent Number: 5,318,015
[45] Date of Patent: Jun. 7, 1994

[54] INHALER HAVING EJECTOR STRUCTURE THAT PROVIDES PRIMARY AND SECONDARY ATOMIZATION OF AN ACTUATED DOSE OF MEDICAMENT

[76] Inventors: Sven Månsson; Monica Månsson-Steinmetz, both of 145 Belgielei, B-2018 Antwerp, Belgium

[21] Appl. No.: 940,028

[22] Filed: Sep. 3, 1992

[51] Int. Cl.$^5$ ............... A61M 11/00; A61M 15/00; A61M 16/00
[52] U.S. Cl. ................... 128/200.22; 128/200.21; 128/200.23; 128/203.19
[58] Field of Search ............... 128/203.12, 203.15, 128/203.21, 200.21, 200.22, 200.23, 203.19

[56] References Cited

U.S. PATENT DOCUMENTS

| 3,119,561 | 1/1964 | Wilson | 239/305 |
| 4,114,615 | 9/1978 | Wetterlin | 128/203.15 |
| 5,009,161 | 4/1991 | Wirz | 101/425 |
| 5,094,165 | 3/1992 | Sugiyama et al. | 101/378 |
| 5,111,744 | 5/1992 | Wieland | 101/486 |

FOREIGN PATENT DOCUMENTS

| 191636 | 8/1988 | Japan | 101/415.1 |
| 1577796 | 7/1990 | U.S.S.R. | 128/203.15 |
| 9007351 | 7/1990 | World Int. Prop. O. | 128/203.15 |
| 9106333 | 5/1991 | World Int. Prop. O. | 128/203.15 |

OTHER PUBLICATIONS

Test Report of The Swedish Handicapp Institute For the "Pari Inhailerboy", Apr. 17, 1985.
Advertisement For DeVilbiss "Ultra-Neb 99" Nebulizer, 1988.
Advertisement For the DeVilbiss "Pulmo-Aide" Nebulizer, 1988.

Primary Examiner—Edgar S. Burr
Assistant Examiner—Kimberly L. Asher
Attorney, Agent, or Firm—Jeffrey Slusher

[57] ABSTRACT

A medicine inhaler has a main body, to which a source of pressurized gas and a source of medicine are attached. By depressing a valve, compressed air enters an ejector through a main channel and atomizes medicine that is drawn into an atomization region by the compressed air. When a piston is in a lower position, into which it is biased by a spring, medicine is free to run into a dosage chamber but is sealed off from an ejection channel and the environment. When the piston is forced upward by compressed air tapped from the main channel, the dosage chamber is sealed off from the medicine source before the dosage chamber is raised to a position in which it communicates with the ejection chamber. When the piston returns to the lower position it generates a secondary puff of air, which enters the main channel to atomize and force residual medicine to the patient. A return channel is also provided to return post-atomized and condensed or improperly atomized medicine to the dosage chamber. Both a portable and a stationary embodiment is provided.

14 Claims, 4 Drawing Sheets

INHALER HAVING EJECTOR STRUCTURE THAT PROVIDES PRIMARY AND SECONDARY ATOMIZATION OF AN ACTUATED DOSE OF MEDICAMENT

BACKGROUND OF THE INVENTION

1. Field of the Invention

This invention relates to an inhaler for delivering medicine to a patient.

2. Description of Related Art

A widespread way to administer medicine to a patient is by using a device that atomizes the drug, which the patient then inhales via a mouthpiece, mask, or hood. Such "inhalers" or "nebulizers" are disclosed in the following texts:

U.S. Pat. No. 3,658,059 (Steil), Apr. 25, 1972;
U.S. Pat. No. 4,007,238 (Glenn), Feb. 8, 1977;
U.S. Pat. No. 4,116,387 (Kremer) Sep. 26, 1978;
U.S. Pat. No. 4,674,491 (Brugger) Jun. 23, 1987; and
U.S. Pat. No. 4,746,067 (Svoboda), May 24, 1988.

In order for an inhaler to be usable and effective for a wide variety of applications, patients, and locations, an inhaler should ideally have the following characteristics:

1. The degree of atomization should be high. In other words, as much of a dose as possible should consist of particles as small as possible.

2. The medicine that is stored in the device should never come in contact with the surrounding air or this contact should at least be kept to a minimum. Such a feature would insure that the medicine would not evaporate or become contaminated or diluted and it would also guarantee that medicine, which is often very expensive or in very limited supply (such as certain known drugs used to treat AIDS patients), is not wasted. Moreover, proper containment also avoids exposing others to the medicine. The medicine should be effectively shielded against contamination up until the moment at which it is atomized.

3. It should be possible to administer medicine in both liquid and powder form.

4. The device should protect the patient from an overdose. In many conventional systems, medicine is atomized when the patient or operator presses some form of "trigger", which then causes compress air to be channeled to an atomization chamber or region within the device. In many known inhalers of this type, medicine is administered to the patient as long as the trigger is depressed. This means that the patient or operator must know when to release the trigger in order to stop the flow of air and end the "dose".

5. Atomized medicine that remains in or has just left the mouthpiece, mask, or hood, or which is still trapped in some cavity of the device, should not be wasted. Such a feature would be of particular importance for patients with breathing difficulties such as those with severe asthma, or unconscious patients.

6. It should be possible to use the inhaler with little or no modification for different types of medicine in order to reduce the cost of using such inhalers, and also for it to have the widest possible area of use.

7. The patient should not need different systems when she is stationary (for example, in a hospital bed) and when she is moving around. The ability to mount an inhaler in a stationary configuration benefits not only individual patients who must remain in the home or hospital, such as AIDS patients, but it is also particularly useful for implementing mass vaccination schemes. A portable inhaler that is also designed to allow easy adaptation to efficient stationary mounting and operation could then be transported to remote or underdeveloped areas.

8. The inhaler should provide effective treatment but should not be cumbersome, and it should be as quite as possible in operation so as not to inconvenience or embarrass the user or disturb others.

9. An inhaler should function simply and it should be easy to take apart and put together. This increases reliability and also promotes and facilitates and easy cleaning.

10. In order to ensure maximum hygiene, it should be possible to clean or sterilize the inhaler in, for example, an autoclave.

Existing inhalers or "nebulizers", such as those described in the patents listed above, fail to meet one or more of the preceding design goals. It is accordingly an object of this invention to provide an inhaler that meets these goals.

SUMMARY OF THE INVENTION

According to the invention, a medicine inhaler is provided that has a main body, to which a source of pressurized gas and a source of medicine are attached. In a portable embodiment, the sources of gas and medicine are provided in containers that mount onto or in the main body. In a plug-in embodiment, the sources are external, whereby they are connected to the main body by hoses and conventional fittings.

By depressing a valve, compressed air (or other gas) from the pressurized gas source enters an ejector through a main channel and atomizes medicine that is drawn into an atomization region by the compressed air. When a piston or similar movable member is in a lower position, into which it is biased by a resilient member, medicine is free to run into a dosage chamber but is sealed off from an ejection channel and the environment.

When the movable member is forced upward by compressed air tapped from the main channel, the dosage chamber is sealed off from the medicine source before the dosage chamber is raised to a position in which it communicates with the ejection chamber. When the movable member returns to the lower position it generates a secondary puff of air, which enters the main channel to atomize and force residual medicine to the patient.

A return channel is preferably also provided to return post-atomized and condensed or improperly atomized medicine to the dosage chamber.

DETAILED DESCRIPTION

Figure 1:
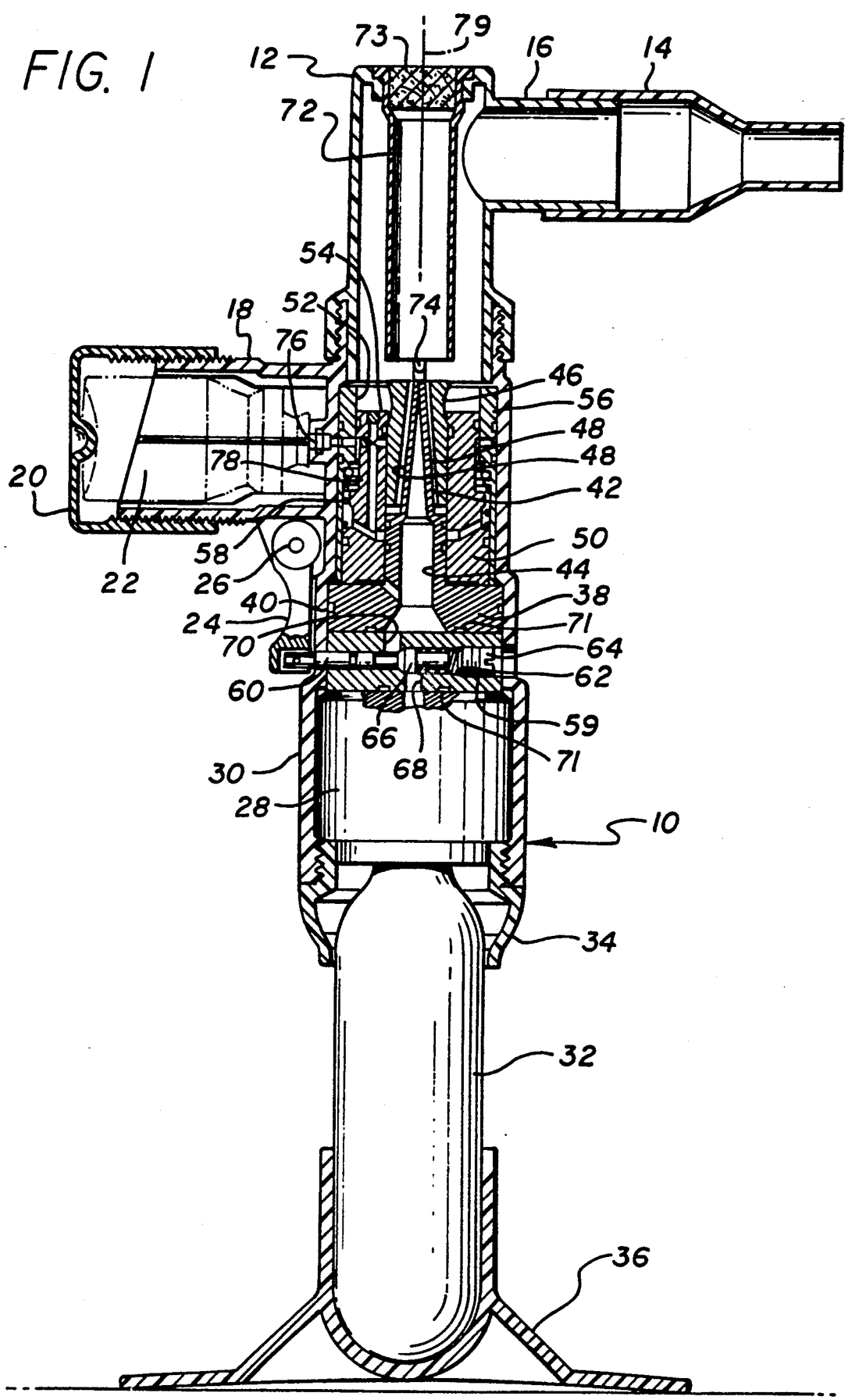
FIG. 1 is a vertical cross-sectional view of one embodiment of an inhaler according to the invention.

FIG. 1 illustrates a portable embodiment of an inhaler according to the invention. The inhaler includes a main body 10, which is preferably made of a synthetic material with sufficient resistance to heat that it will withstand the temperatures normally found in an autoclave. Another advantage of using a synthetic material for the main body 10 is that it can be easily injection molded using known techniques. It is also possible, however, to manufacture the main body 10 of metal. The main body 10 is generally cylindrical and is open at its top and bottom in the illustrated embodiment.

A cap 12, which is preferably made of the same material as the main body 10, is fitted onto the top of the main body 10. By providing the main body 10 and cap 12 with mating threads, the cap 12 can be mounted on the main body 10 by screwing it onto the top of the main body. Other arrangements are also possible, for example, a snap-on fitting.

A mouthpiece 14 is attached to the cap 12, for example, via a generally cylindrical connecting portion 16 that opens into the interior of the cap 12. It is also possible to make the mouthpiece 14 an integral portion of the cap 12, but fitting a separate mouthpiece 14 onto the cap 12 will normally be a more hygienic alternative since it allows the mouthpiece 14 to be removed for cleaning or even replaced. A removable mouthpiece 14 is of course desirable when more than one patient is to use the inhaler.

The main body 10 also has a generally cylindrical connecting portion 18, preferably on the side of the main body 10 opposite the mouthpiece 14 so as not to be in the way of the user's hand during operation of the inhaler. A cap 20 screws down or snaps onto the connecting portion 18. A medicine container 22 fits within the connecting portion 18 and the cap 20. The container 22 may be of any conventional material including plastic, metal, and glass. It may be pressurized, and the medicine may be in either liquid or powder form.

A trigger 24 is mounted on the main body 10 and can pivot about a shaft 26. The trigger 24 is preferably mounted on the side of the main body 10 opposite the mouthpiece 14 so that the user can squeeze the trigger 24 with her index or middle finger while holding the inhaler comfortably in her hand. It is, however, also possible to mount the trigger on the same side of the inhaler as the mouthpiece 14, whereby the user could press in the trigger 24 with her thumb. The arrangement of such triggers on inhalers is well known and is therefore not described further. It is also possible to vary the construction or mounting of the trigger in any conventional manner.

In this embodiment, a conventional pressure regulator 28 is housed within a lower portion 30 of the main body 10. A conventional cartridge 32 containing a compressed propellant gas or mixture is connected in a conventional manner to the known regulator 28. By way of example only, it is assumed below that the cartridge contains compressed and preferably medically pure air. Other gases may be used, however, including oxygen, and the air or other gas may itself also contain some medication.

A collar 34, which may screw, snap, or otherwise fit into or onto the lower portion 30 of the main body 10, also extends around the cartridge 32 to help align and stabilize it. The collar 34 also helps to keep dirt, dust, and other foreign particles out of the cavity in the main body 10 where the cartridge 32 is connected to the regulator 28.

A foot 36 is preferably provided for mounting onto the bottom of the cartridge 32, so that the user can set the inhaler aside. Because the inhaler according to the invention effectively seals off all pathways through which the medicine could run out of the inhaler, no medicine will be lost even if the inhaler is not standing vertically. The foot 36, however, helps prevent the inhaler from falling and enables the user to grasp the inhaler securely and rapidly, for example, in the case of an acute attack of asthma.

The foot 36 may alternatively be formed as a combination bottom cap and support so as to completely enclose the cartridge 32. In such case, the bottom cap and foot 36 could replace the collar 34, in which case the bottom cap could screw into or onto the lower portion 30 of the main body 10.

The main body 10 also houses an ejector that includes an inner member 38, which is sealed against the inner surface of the main body 10, preferably via a sealing member such as an O-ring 40. The inner ejector member 38 has a mainly disk-shaped base portion and a central tapered portion 42 that extends upward. A central channel 44 extends through the base portion of the inner ejector member 38 and through the tapering portion 42. The central channel 44 thus extends all the way through the inner ejector member 38 and is the main channel through which the compressed air from the cartridge 32 flows to atomize and transport the medicine.

The ejector also includes an outer member 46 that surrounds and bears against the outer surface of the upper tapered portion 42 inner ejector member 38 but has at least one and preferably at least a pair of grooves 48 that extend along the inner ejector member to form upwardly converging channels. Medicine ejection channels 48 are thereby formed along the outside of the mainly conical upper section of the tapering portion 42 of the inner ejector member 38. The ejection channels 48 open upward into the cavity formed in the interior of the cap 12.

A mainly cylindrical piston member 50 extends around the tapering portion 42 of the inner ejector member 38 and around the outer ejector member 46, but is not as high as the tapering portion 42 of the inner ejector member; a cavity 52 is thereby formed above the upper surface 54 of the piston 50 at the base of the cap 12. The upper surface 54 of the piston 50 is preferably sloped so that liquid or solid material in the cavity 52 will tend to run inward toward the outer ejector member 46.

A sleeve 56 surrounds the piston 50 and seals the inner wall of the main body 10 against the outer surface of the piston 50. An annular channel is formed between the piston 50 and the sleeve 56 between where these two elements are sealed against each other, preferably using conventional O-rings. This annular channel is described in greater detail below.

A spring 58 bears upward against an annular seat formed in the sleeve 56 and downward against the piston 50. The spring 58 biases the piston downward toward the base portion of the inner ejector member 38. Other biassing members and arrangements may also be used. For example, the spring or some other resilient element could be mounted in the cavity 52 above the piston and be configured to bias the piston downward.

Communication between the central channel 44 in the inner ejector member 38 and the outlet from the pressure regulator 28 is controlled by a spring-biased valve that is mounted within an intermediate connecting member 59. This connecting member 59 is generally disk-shaped or cylindrical, and has a lateral bore in which a valve stem 60, a spring 62, and a sealing portion or element 64 are mounted.

The lateral bore has a first portion whose diameter is smaller than a second portion. The larger-diameter portion is preferably rounded or tapered inward at the junction with the smaller-diameter bore portion to provide a bearing surface against which the sealing portion or element 66 seats when in the closed-off position shown in FIG. 1.

A first vertical opening 68 connects the outlet from the regulator 28 with the larger-diameter portion of the lateral bore and a second vertical opening 70 connects the smaller-diameter portion of the lateral bore with the central channel 44 in the inner ejector member 38. Leakage from the openings and mating surfaces around the openings 68, 70 is preferably prevented by conventional sealing members such one or more 0-rings 71 between the mating surfaces and surrounding each opening 68, 70.

The sealing portion 66 of the valve stem blocks communication between the vertical openings 68, 70 when in position between these openings. When the valve stem 60 is pressed in (viewed as in FIG. 1, to the right) until the smaller-diameter portion of the valve stem is between the openings 68, 70, the sealing portion 66 allows communication between the openings 68, 70, and compressed air can flow around the smaller-diameter portion from the first opening 68 to the second opening 70.

The spring 62 is pre-tensioned so as to bias the valve stem to the left (viewed as in FIG. 1). In other words, the spring 62 tends to force the sealing portion 66 of the valve stem into the position that blocks communication between the vertical openings 68, 70. The sealing portion 66 is therefore preferably tapered to seat against the rounded or tapered bearing surface at the juncture between the larger and smaller-diameter portions of the lateral bore. A headless screw or other fastener 64 is preferably mounted through an opening in the main body 10 and screws into the intermediate connecting member 59 not only to form a second bearing surface for the spring 62, but also to allow the valve assembly to be removed for cleaning and easily installed.

Other valve arrangements may be used. For example, a single-diameter shaft with a lateral through-hole may be used, whereby the openings 68, 70, which could then be aligned, are brought into communication only when the valve stem is pressed far enough in for the through-hole to line up with the openings.

A mainly cylindrical air intake member 72, which may optionally be molded as an integral portion of the cap 12, opens at the top of the cap to the surrounding atmosphere and extends downward within the cap to open above the outer ejector member 46. The intake opening allows air to enter the cap 12 so as to prevent overpressure or underpressure within the cap impeding the effective atomization and ejection of medicine within and from the inhaler. If other conventional methods are used to equalize pressure, the opening through the intake member 72 can be sealed or eliminated. As is illustrated below with reference to a plug-in embodiment of the invention, an external source of oxygen or other gas may also be attached to the intake member 72 to seal the inhaler while still allowing for pressure equalization.

A filter or filter plug 73 is preferably inserted into or over the intake member 72. The filter 73 may be of any suitable type, both active and passive, and is provided to filter contaminants from the air that enters the inhaler through the intake member 72.

An atomizing bead 74 is also mounted close to and above the upper opening of the tapering portion 42 of the inner ejector member 38 and near the lower opening of the air intake member 72. This bead has preferably rounded bottom edges so as to more effectively separate and channel atomized medicine.

Medicine from the container 22 enters the inhaler via a conventional sealed valve 76 so that medicine can flow into an outer channel 78 between the sleeve 56 and the piston 50. The configuration of the outer channel 78 is described and illustrated in greater detail below.

Figure 3:
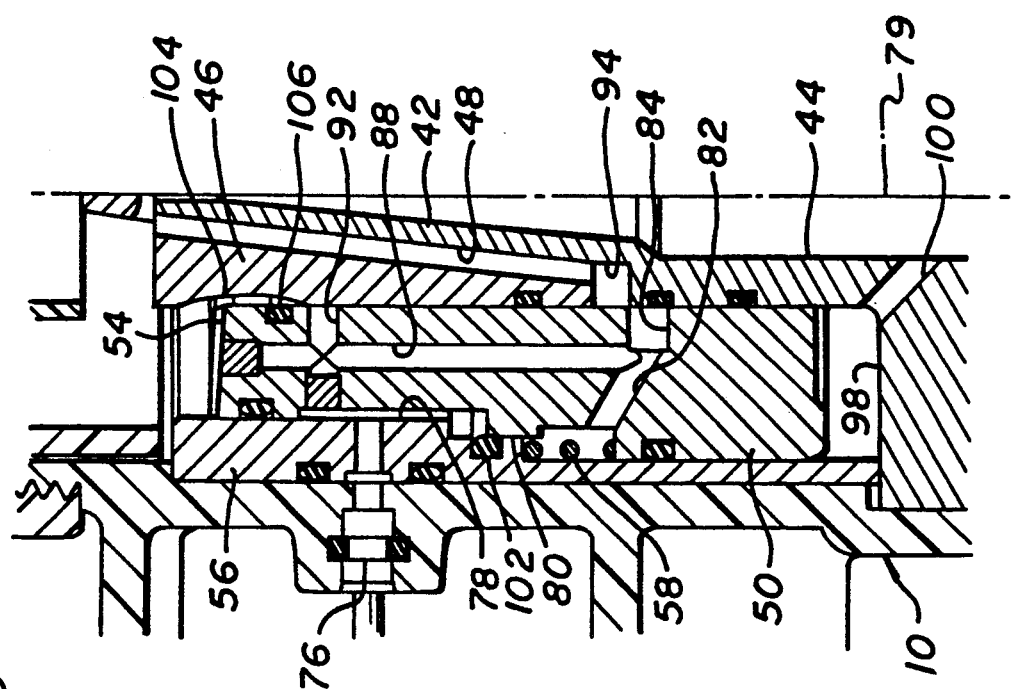
FIGS. 2–4 show, sequentially, a valve and channel arrangement according to a preferred embodiment of the invention in different operating positions over the course of administering one dose of medicine using the inhaler.
Figure 2:
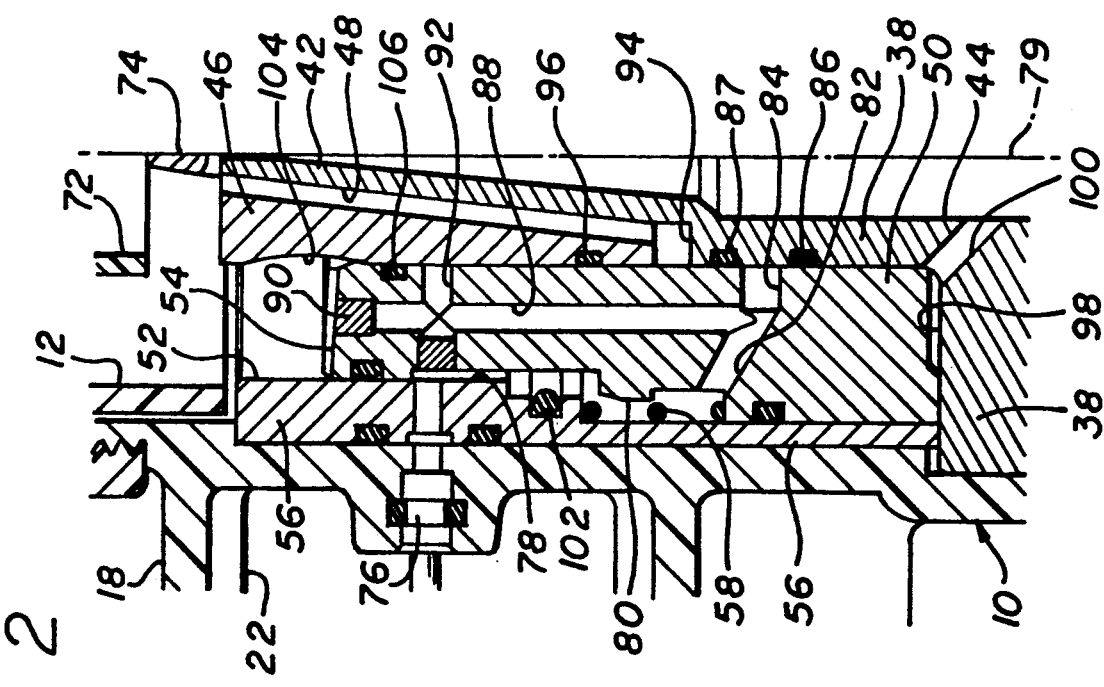
Figure 4:
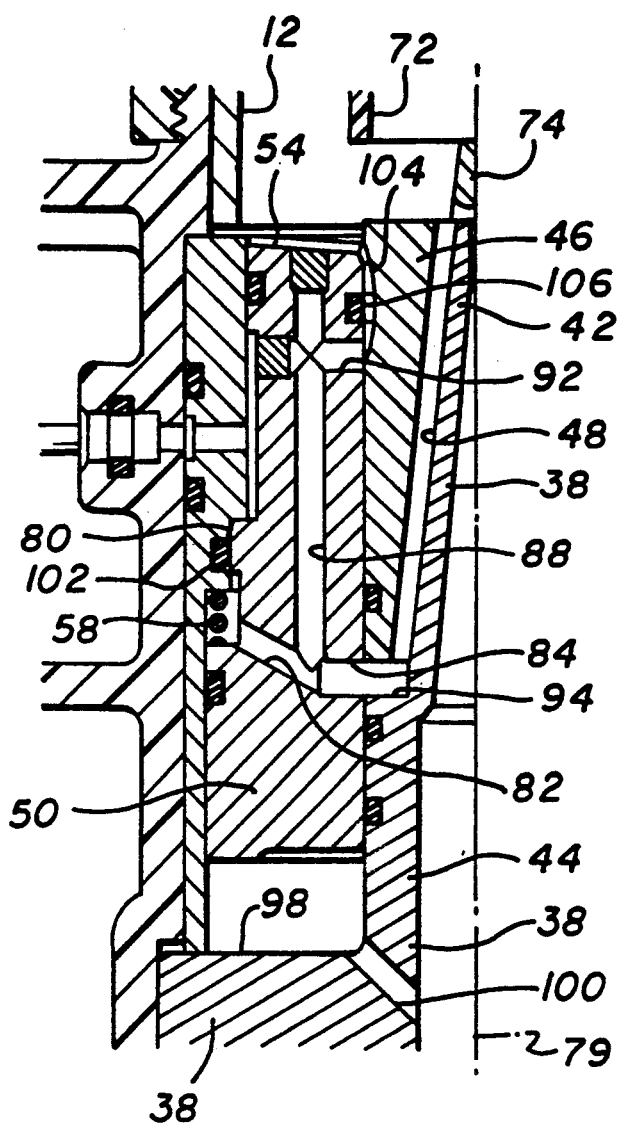
Figure 5:
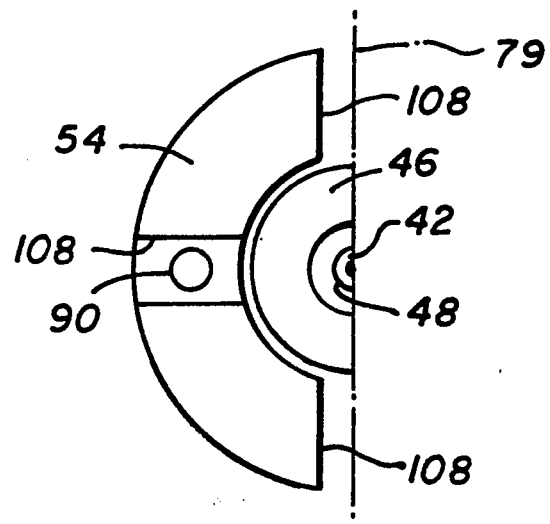
FIG. 5 is a top view of one side of an ejector configuration that allows for collection and reuse of atomized and condensed medicine.

FIG. 2 is an enlarged cross-sectional, partial view of the dosage and injection assembly to the left of a centerline 79 (see FIG. 1) of the device. As FIG. 2 illustrates, medicine enters the inhaler via the valve 76, whereby the points of passage between mating surfaces are sealed by O-rings. As FIG. 1 illustrates, except for the valve 76 and its fittings, the structure of the dosage and injection assembly is preferably substantially symmetrical about the centerline 79. It is therefore to be understood that, with certain indicated exceptions, the various structural features described in the singular below with reference to FIGS. 2-4 are preferably included on both sides of the centerline, and may even be more than two in number and distributed angularly about the centerline.

Upon entering the inhaler, the medicine flows into the outer channel 78 between the sleeve 56 and the piston 50, downward past the spring 58 and a sealing protrusion 80 on the piston 50, and further down to a downward-sloping base channel 82 that extends inward through the piston and opens into an inlet chamber 84. When the piston is in its lowest position, in which it bears against the inner ejector member 38 (or, alternatively, against an inward-facing protrusion of the sleeve 56 or the main body 10, the inlet chamber 84 is sealed off by an O-ring 86 so that no medicine can leak between the piston 50 and inner ejector member 38.

A vertical channel 88 is also made in the piston 50. This vertical channel 88 extends preferably from near the top of the piston and downward within the piston until it opens into the base channel 82 or the inlet chamber 84. The vertical channel 88 does not open into the cavity 52 formed above the piston when the piston is in its lowest position as shown in FIG. 2. In order to make manufacturing easier, the vertical channel 88 may be made in the piston by drilling a hole down through it and then sealing it at the top, for example, by welding shut the upper opening, by attaching a cap over the piston 50, or by using a plug 90, or the like.

A horizontal channel 92 is also formed in the piston 50 and connects the vertical channel 88 with the surface of the outer ejector member 46. The outer end (to the left, viewed as in FIG. 2) of the horizontal channel 92 is sealed.

The ejection grooves or channels 48 formed between the outer surface of the inner ejector member 38 and the inner surface of the outer ejector member 46 are open to the outer surface of the piston 50 via an outlet chamber 94. Leakage from the outlet chamber 94 between the piston 50 and inner and outer ejector members 36, 46 and the piston 50 is prevented using conventional elements such as an O-rings 87 and 96.

The radially inward portion of the bottom surface of the piston 50 is preferably slightly recessed so as to form a compression chamber 98 between the bottom surface of the piston 50 and the upper surface of the base of the inner ejector member 38. This compression chamber 98 is connected with the central channel 44 in the inner ejector member 38 via a lower channel 100.

FIG. 2 shows the ejection mechanism of the invention in its at-rest state. In this at--rest state, medicine can flow into and fill the outer channel 78, the base channel 82, and the inlet chamber 84, but it is sealed off from the outlet chamber 94 so that it cannot reach the ejection channels 48 and be forced out to the surrounding environment or to the mouthpiece (see FIG. 1). Some medicine may also rise within the vertical channel 88, although, since this channel is sealed everywhere except at the bottom, the vertical channel 88 will, in general, not fill with medicine. Furthermore, while the medicine is in the ejection system, it is completely sealed off from the environment and the surrounding air.

Referring now to all of FIGS. 1–4, assume that the user presses in on the trigger 24 so that the valve moves to the right. Compressed air can then flow from the cartridge 32 and the regulator 28, through the first vertical opening 68 and the second vertical opening 70 and into and out the top of the central channel 44. This rise in pressure will also be transmitted to the bottom of the piston 50 as the compressed air flows through the lower channel 100 and into the compression chamber 98. The piston 50 will then be forced upward against the force of the spring 58.

Before the piston 50 rises far enough for the inlet chamber 84 to communicate with the outlet chamber 94, the sealing protrusion 80 of the piston 50 will reach the O-ring 102. The portion of the outer channel 78 above the O-ring 102 will then be sealed off from the portion of the outer channel below the O-ring 102.

One dose of medicine is therefore the amount that is located below the O-ring 102 in the channel 78, in the base channel 82, in the inlet chamber 84, and in the lower portion of the vertical channel 88. These channels and the chamber 84 therefore form a dosage cavity, and the amount of medicine contained in one dose can therefore be determined with great accuracy ahead of time simply by calculation or by measuring the amount of liquid in the dosage cavity. Moreover, the amount of medicine in one dose will not change, regardless of the type of medicine used, the number of times the inhaler is operated, or the degree of pressurization in the cartridge 32.

As the piston is forced farther upward, the two chambers 84, 94 will align or will at least open into one another. Referring to FIG. 1 and 4, as the compressed air rushes out of the constricted upper opening of the tapered portion 42 of the inner ejector member 38, the air pressure in this region will drop and will suck the medicine out of the outer channel (below the O-ring 102), the base channel 82, the vertical channel 88, and the chambers 84, out through the chambers 94, and up through the ejection channels 48. When the medicine exits the channels 48, it will be mixed with the compressed air, and will be atomized in the conventional manner, whereby it will then pass out of the inhaler through the mouthpiece 14 and to the patient. One prototype of the invention achieved 90% atomization, with particles no greater than 6$\mu$.

Notice that the amount of medicine administered will be the same no matter how long the user holds in the valve stem 60 via the trigger 24: the medicine in the container 22 is sealed off from the ejection channels 48 by the O-ring 102, and the only effect of holding in the trigger too long will be that some of the air or gas in the cartridge 32 will be wasted. If more medicine is needed or has been prescribed, the user can release the trigger, whereby more medicine will flow down toward the inlet chamber 84, and she can then press the trigger in again. A complete treatment can then be defined by specifying the number of "shots" need, that is, the number of times the user must press and release the trigger.

As FIG. 2 shows, an O-ring 106 seals off the horizontal channel 92 from the cavity 52 above the piston 50. Referring also to FIGS. 3 and 4, the horizontal channel 92 comes into communication with the space above the piston 50 when the piston rises to a point at which the O-ring 106 is adjacent to a recessed or tapered portion 104 of the outer surface of the outer ejector member 46. In this position, a gas, liquid, or powder is free to run down from the cavity 52 (which is made easier by the upper surface of the piston sloping inward), between the outer ejector member 46, past the O-ring 106 and into the horizontal channel 92.

Allowing the horizontal channel 92 to communicate with the cavity 52 also equalizes the pressure within the piston 50 and thus allows the medicine included in the dose to be pumped with full effect.

When the compressed air is shut off (the user releases the trigger 24), the spring 58 will force the piston 50 downward until the O-ring 106 is located below the recessed portion 104, where it seals the piston 50 against the outer surface of the outer ejector member 46. At this point, the horizontal and vertical channels 88, 92 will once again be sealed off from the space above the piston 50.

FIG. 5 is a view from above of the sloped top surface of the piston 50, the top of the outer ejector member 46, and the top of the tapered portion 42 of the inner ejector member 38. As FIG. 5 illustrates, the sloped top surface 54 of the piston 50 preferably has slits or grooves 108 that allow any material that collects above the piston to run down into the gap between the piston 50 and the outer ejector member 46. Assume for example that droplets or other particles of medicine have condensed or otherwise collected on the walls or in the cavity under the cap. These particles or drops will then run down onto the sloped upper surface 54 of the piston 50 and will drain down into the gap between the piston 50 and the outer ejector member 46 (at the recessed portion 104) and down into the horizontal channel 92 and the vertical channel 88. This "recycling" feature avoids wasting any medicine.

The vertical and horizontal channels 88, 92 are provided to connect the cavity 52 above the piston 50 with the inlet chamber 84 so that condensed or recaptured droplets or particles will be able drain back down through these channels and into the chamber 84. Note that each of these channels is substantially parallel to at least one side of the piston 50. As such, it will generally be easy to bore through the piston or mold it such to create the two separate channels and then to seal one end of each. Separate channels 88, 92 are not necessary, however; instead, a single channel extending, for example, diagonally down from an opening below the O-ring 106 to the base channel 82, inlet chamber 84, or even the outer channel 78 could be provided. In such case, it would not be necessary to plug or seal any end of any channel.

Assume now that the user releases the trigger 24 so that the flow of compressed air from the cartridge 32 is cut off. The spring 58 will then quickly force the piston 50 downward toward the base of the inner ejector member 38. The air or other gas in the space 98 beneath the base of the piston 50 and the upper surface of the base of the inner ejector member 38 will then be forced out through the lower channel 100 and up through the central channel 44.

This secondary "puff" of air will accelerate over the length of the tapering portion 42 of the inner ejector member 38, will be separated by the preferably sloped lower surface of the atomization bead 74, and will be directed upward through the cap and out through the mouthpiece 14. This secondary pumping action not only increases the exit velocity of the atomized medicine, but it also significantly improves the ability of the medicine to penetrate into the patient's lungs. Furthermore, the secondary pumping action increases the amount of medicine in a given dose that actually is pumped out to the patient.

Another advantage of the inhaler according to the invention is that it will typically be very quiet since there are only a very few moving parts and the compressed air or other propellant needs to make very few eddy-building turns as it flows from the cartridge 32 to the mouthpiece 14.

Referring once again to FIG. 1, note that the outer channel 78 and the base channel 82 preferably extend around much or most of the entire piston 50. The angular extent of these medicine-collecting channels can be varied, depending on the size of doses that the inhaler is designed to administer. The vertical and horizontal channels 88, 92, however, need only be formed in the piston adjacent to the medicine container 22.

Figure 6:
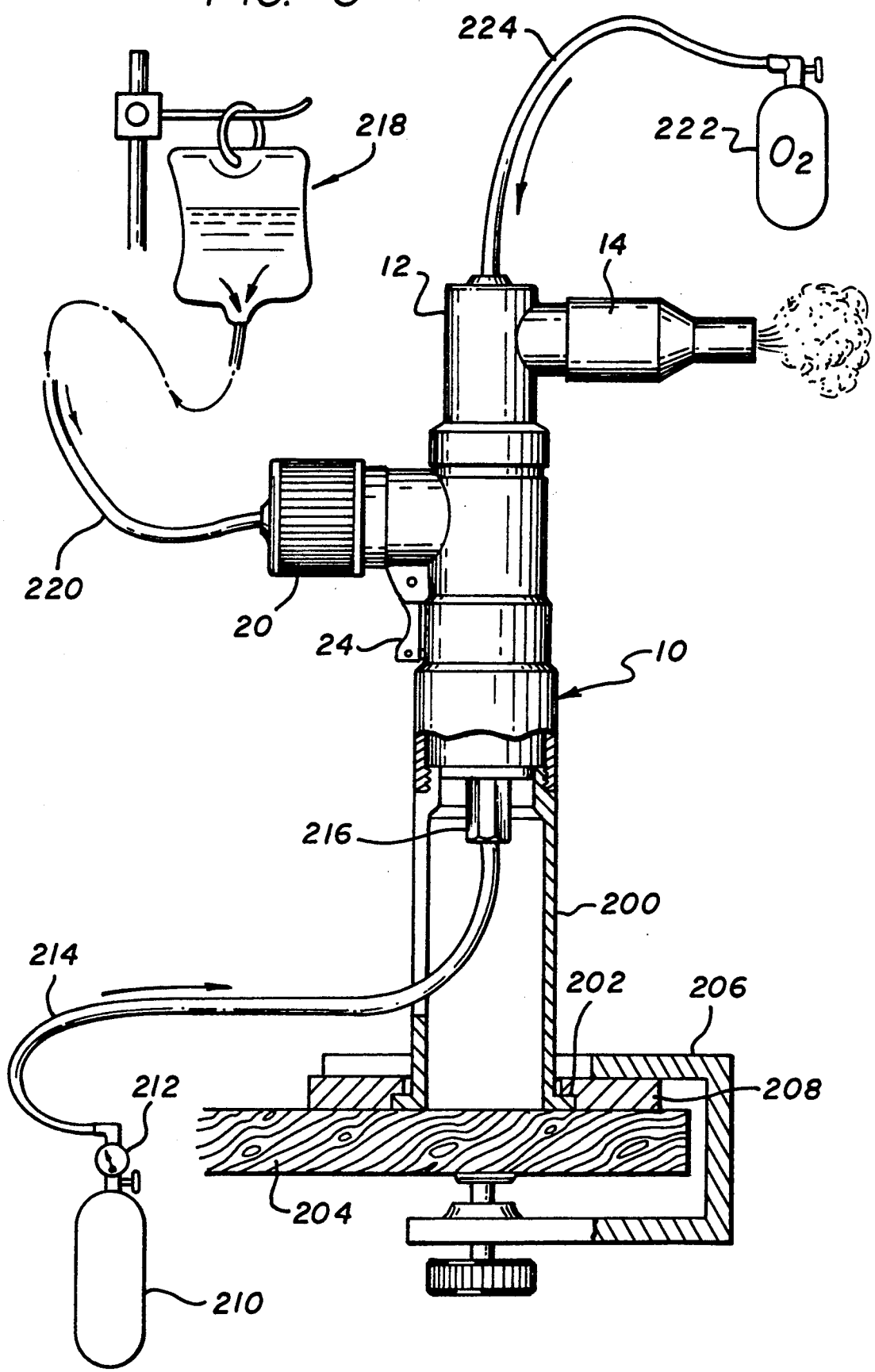
FIG. 6 illustrates a "plug-in" stationary embodiment of the inhaler according to the invention.

FIG. 6 illustrates a plug-in version of the invention that is particularly suitable for use in applications such as mass vaccination, in remote areas, and for treatment in highly contaminated areas. In this version, a mainly cylindrical foot 200 is connected directly to the main body 10. A flange 202 is provided at the base of the foot 200, and the inhaler can be mounted on a table or other surface 204 using any conventional means, such as a clamp 206, possibly with spacers 208, or by other means such as screws or other fasteners through the flange 202.

In this "plug-in" embodiment, medically pure air or other compressed gas is supplied via an external source such as a container 210 and a pressure regulator 212 and a hose or other connector 214 and is connected to the first opening 68 (see FIG. 1) of the inhaler using a conventional air-tight fitting 216. The external container 210 and regulator 212 thus replace the cartridge and regulator 32, 28 in the portable embodiment shown in FIG. 1.

Similarly, medicine is supplied to the inhaler from an external source such as a conventional IV bag 218. The medicine is, for example, gravity-fed through a hose 220 and into the inhaler via a conventional fitting. The container 218 and hose 220 thus replace the container 22 in the portable embodiment.

In order to completely eliminate the risk of contaminating atomized medicine through contact with the atmosphere within the cap 12, lightly pressurized oxygen is preferably supplied to the chamber within the cap 12 from an external source such as a tank 222 and through a connecting hose 224.

The operation of this plug-in embodiment of the invention and the configuration of the various channels and moving and fixed members of the ejector within the main body 10 may be the same as in the portable embodiment shown and described above. The more complicated internal parts of the inhaler can therefore be the same in both embodiments. This reduces manufacturing costs and makes it easier to convert one embodiment to the other. Depending upon the conventional fittings used to connect the medicine source and compressed air to the inhaler, it is also possible for the same inhaler to be quickly converted from one embodiment to the other; the internal workings of the device will be the same.

We claim:
1. An arrangement for delivering medicine to a patient comprising:
a main body;
a medicine source attached to the main body;
a source of pressurized atomization gas attached to the main body;
a medicine outlet;
valve means with a blocking position and a connecting position;
an inner ejector member;
an outer ejector member;
a main channel that extends through the inner ejector member;
at least one medicine ejection channel formed between the inner and outer ejector members;
a movable member that has a first position and a second position, that is substantially cylindrical, and that is located radially outward from the inner and outer ejector members;
resilient means for biasing the movable member into the first position;
a dosage cavity formed within the movable member; and
dosage sealing means for permitting communication between the dosage cavity and the medicine source when the movable member is in the first position and for sealing off the medicine source from the dosage cavity when the movable member is in the second position;
in which:
when the valve means is in the blocking position, the source of atomization gas is sealed off from the main channel, the medicine source is in communication with the dosage cavity, the dosage cavity is sealed off from the ejection channel, and the movable member is biased into the first position; and
when the valve means is in the connecting position, the source of atomization gas is in communication with the main channel, the medicine source is sealed off from the dosage cavity, the dosage cavity is in communication with the ejection channel, and the movable member is in the second position, whereby medicine located in the dosage cavity is atomized by the atomization gas at an atomization opening and is forced through the outlet.

2. An arrangement as defined in claim 1, in which:
a compression chamber is located between the movable member and the inner ejector member;
a lower channel is formed in the inner ejector member and connects the compression chamber with the main channel;

whereby the movable member is urged into the second position by the pressure of the pressurized atomization gas against the biasing force of the resilient means when the valve means is in the connecting position.

3. An arrangement as defined in claim 2, in which the compression chamber forms a secondary source of atomization gas, whereby atomization gas within the compression chamber when the movable member is in the second position is forced through the lower chamber and through the main channel when the valve means switches from the connecting to the blocking position and the resilient means biases the movable member into the first position.

4. An arrangement as defined in claim 1, in which:
   a collection chamber is located above the movable member;
   a return channel with an upper and a lower opening is provided in the movable member;
   the lower opening of the return channel opens into the dosage cavity; and
   return sealing means is provided for sealing off the upper opening of the return channel from the collection chamber when the movable member is in the first position and for opening a connection between the return channel and the collection chamber when the movable member is in the second position;
   whereby post-atomized medicine drains back into the dosage cavity when the movable member is in the second position.

5. An arrangement as defined in claim 4, in which the moving member has an inward-sloping upper surface forming a drainage surface leading to the return channel.

6. An arrangement as defined in claim 1, in which the dosage sealing means is provided for sealing off the medicine source from the dosage cavity before the dosage cavity comes into communication with the ejection channel as the movable member moves from the first position to the second position.

7. An arrangement as defined in claim 6, in which the dosage sealing means comprises a protruding portion of the movable member and a resilient sealing element mounted in an outer wall of the dosage cavity, whereby the protruding portion is in contact with and seals against the sealing element whenever the dosage chamber is in communication with the ejection chamber.

8. An arrangement as defined in claim 1, further including:

valve biasing means for biasing the valve means into the blocking position; and trigger means in contact with the valve means for biasing the valve means into the connecting position.

9. An arrangement as defined in claim 1, in which the medicine outlet is a mouthpiece.

10. An arrangement as defined in claim 1, in which the source of atomization gas is a pressurized gas container attached to the main body.

11. An arrangement as defined in claim 1, in which the resilient means is a spring located within the dosage chamber.

12. An arrangement as defined in claim 11, further including an external air intake opening connecting an interior region of the cap with the atmosphere.

13. An arrangement as defined in claim 1, further including:

a cap that is attached to a top portion of the main body; and in which:

the outlet opens into an interior region of the cap;

the main channel and ejection channels open into the interior region of the cap; and the ejection channel forms an annular opening in the inner ejector member surrounding an upper opening of the main channel.

14. A medicine inhaler including:

a main body;

a medicine source attached to the main body;

a source of pressurized atomization gas attached to the main body;

a mouthpiece forming a medicine outlet;

valve means with a blocking position and a connecting position;

valve biasing means for biasing the valve means into the blocking position;

trigger means in contact with the valve means for biasing the valve means into the connecting position an inner ejector member;

a main channel extending through the inner ejector member;

an outer ejector member;

a medicine ejection channel extending between the inner ejector member and the outer ejector member;

a movable member with a first position and a second position;

resilient means for biasing the movable member into the first position;

a dosage cavity formed within the movable member; and dosage sealing means for permitting communication between the dosage cavity and the medicine source when the movable member is in the first position and for sealing off the medicine source from the dosage cavity when the movable member is in the second position; and a cap that is attached to a top portion of the main body;

in which:

the mouthpiece opens into an interior region of the cap;

the main channel and ejection channels open into the interior region of the cap;

the ejection channel forms an annular opening in the inner ejector member surrounding an upper opening of the main channel;

when valve means is in the blocking position, the source of atomization gas is sealed off from the main channel, the medicine source is in communication with the dosage cavity, the dosage cavity is sealed off from the ejection channel, and the movable member is biased into the first position; and when the valve means is in the connecting position, the source of atomization gas is in communication with the main channel, the medicine source is sealed off from the dosage cavity, the dosage cavity is in communication with the ejection channel, and the movable member is in the second position, whereby medicine located in the dosage cavity is atomized by the atomization gas at an atomization opening and is forced through the outlet;

a compression chamber is located between the movable member and the inner ejector member;

a lower channel is formed in the inner ejector member and connects the compression chamber with the main channel whereby the movable member is urged into the second position by the pressure of the pressurized atomization gas against the biasing force of the resilient means when the valve means is in the connecting position;

the compression chamber forms a secondary source of atomization gas, whereby atomization gas within the compression chamber when the movable member is in the second position is forced through the lower chamber and through the main channel when the valve means switches from the connecting to the blocking position and the resilient means biases the movable member into the first position;

a collection chamber is located above the movable member;

a return channel with an upper and a lower opening is provided in the movable member;

the lower opening of the return channel opens into the dosage cavity;

return sealing means is provided for sealing off the upper opening of the return channel from the collection chamber when the movable member is in the first position and for opening a connection between the return channel and the collection chamber when the movable member is in the second position, whereby post-atomized medicine drains back into the dosage cavity when the movable member is in the second position;

the dosage sealing means is provided for sealing off the medicine source from the dosage cavity before the dosage cavity comes into communication with the ejection channel as the movable member moves from the first position to the second position;

the dosage sealing means comprises a protruding portion of the movable member and a resilient sealing element mounted in an outer wall of the dosage cavity, whereby the protruding portion is in contact with and seals against the sealing element whenever the dosage chamber is in communication with the ejection chamber.

* * * * *